United States Patent [19]

Khorasani

[11] Patent Number: 4,979,937

[45] Date of Patent: Dec. 25, 1990

[54] METHOD AND APPARATUS INVOLVING INTERCOSTAL AND LUMBAR PERFUSION

[76] Inventor: Ahmad R. Khorasani, 609 Canton St., Westwood, Mass. 02090

[21] Appl. No.: 415,909

[22] Filed: Oct. 2, 1989

Related U.S. Application Data

[63] Continuation-in-part of Ser. No. 136,397, Dec. 22, 1987, abandoned.

[51] Int. Cl.$^5$ ............................................. A61M 5/00
[52] U.S. Cl. ........................................ 604/8; 604/174; 604/28; 606/151
[58] Field of Search ...................................... 604/8–10, 604/28, 49, 174, 283, 284; 606/151–158, 221

[56] References Cited

U.S. PATENT DOCUMENTS

| | | | |
|---|---|---|---|
| 3,435,824 | 10/1966 | Gamponia | 604/8 |
| 3,882,862 | 5/1975 | Berend | 604/8 |
| 4,484,911 | 11/1984 | Berlin et al. | 604/174 |
| 4,501,263 | 2/1985 | Harbuck | 604/9 |
| 4,560,375 | 12/1985 | Schulte et al. | 604/9 |
| 4,586,919 | 6/1986 | Taheri | 604/9 |
| 4,592,754 | 6/1986 | Gupte et al. | 604/9 |
| 4,712,551 | 12/1987 | Raghanabad | 604/8 |

Primary Examiner—C. Fred Rosenbaum
Assistant Examiner—Kathleen A. Daley
Attorney, Agent, or Firm—Herbert L. Bello

[57] ABSTRACT

A method and apparatus for providing circulation to distal organs and blood flow for intercostal lumbar perfusion during aortic surgery by means of an intercostal and lumbar perfusion shunt having a main tubular member defining a first flow path and a plurality of side tubular members connected intermediate the ends of the main tubular member and defining a plurality of second flow paths. The method includes the steps of shunting a pathologic section by connecting the free ends of the main tubular member to the aorta proximal and distal to the pathology for providing blood flow to the distal organs and by connecting the free ends of the side tubular members to the intercostals through an opening in the aorta for providing blood flow to the intercostals during surgery.

18 Claims, 7 Drawing Sheets

METHOD AND APPARATUS INVOLVING INTERCOSTAL AND LUMBAR PERFUSION

CROSS-REFERENCE TO RELATED APPLICATIONS

This application is a continuation-in-part application of Ser. No. 136,397, filed Dec. 22, 1989, now abandoned.

BACKGROUND OF THE INVENTION

1. Field of the Invention

The present invention relates to a method and apparatus for providing blood flow during surgical procedures and, more particularly, is directed towards an intercostal lumbar perfusion apparatus and method for providing circulation to distal organs and blood flow to the intercostals during aortic surgery.

2. Description of the Prior Art

Paraplegia is a disastrous complication of aortic surgery which results from ischemia of the spinal cord. This may occur either after application of the cross clamp, if no adjunct is used to provide distal circulation, or after exclusion of the pathologic segment of the aorta with a proximal and distal aortic clamp, when adjuncts like shunt or partial bypass of some sort are employed for maintenance of distal circulation. Use of available techniques to prevent paraplegia are effective only if the major spinal artery is coming off an intercostal in the perfused distal or proximal aorta and the state of the collateral circulation is favorable. Attempts to increase the distal perfusion pressure with partial bypass are not expected to prevent ischemia to the spinal cord in the absence of favorable collateral circulation and distal location of the spinal branch of the posterior intercostals.

Intraoperative monitoring of the spinal cord functions with the use of somatosensory evoked potentials only monitor the functional integrity of the sensory tracts in the posterior spinal cord. Since the collateral circulation between the posterior and anterior spinal arteries varies, ischemic injury to the anterior spinal cord without any damage to the posterior sensory tracts is a possibility. Accordingly, persistent normal intraoperative somatosensory evoked potential, in a given case, does not guarantee absence of postoperative paraplegia. Secondly, in the absence of a secure means for immediate intraoperative reperfusion of the ischemic intercostals, knowledge of changes in somatosensory evoked potentials does not help the patient and may, in fact, force the surgeon to perform a speedy, but inaccurate operation with its associated complications.

Since accurate localization of the spinal branches of the posterior intercostals and details of the collateral circulation cannot be determined preoperatively, a need has arisen for a method and apparatus for preventing paraplegia caused by ischemia to the spinal cord during aortic surgery.

SUMMARY OF THE INVENTION

It is an object of the present invention to provide a method and apparatus for preventing ischemia of the spinal cord during aortic surgery.

It is a further object of the present invention to provide a method and apparatus for intercostal lumbar perfusion during aortic surgery for prevention of paraplegia due to ischemia.

An intercostal lumbar perfusion apparatus made according to the invention has a main tubular member defining a first flow path for providing circulation to distal organs and a plurality of side tubular members defining a second flow path for providing blood flow for intercostal lumbar perfusion during surgery on the descending and thoraco abdominal aorta. The side tubular members interconnect with the main tubular member intermediate the ends thereof to form a path for blood to flow from the first flow path into the second flow path, the diameter of the side tubular members being smaller than the diameter of the main tubular member.

The method of the present invention for providing circulation to distal organs and blood flow for intercostal lumbar perfusion during aortic surgery includes the steps of attaching the main tubular member of an intercostal lumbar perfusion apparatus to the aorta proximal and distal to the pathology, the side tubular members being clamped initially to prevent flow of blood, clamping the aorta between the pathology and the main tubular member connections, blood flowing to the distal organs through the deaired main tubular member, opening the aorta to expose the intercostals selecting the proper size perfusion catheter tip for the particular intercostal and, after deairing this branch, connecting the selected side tubular members tips to the respective intercostals, removing the clamps on the side tubular members and permitting blood to flow to the intercostals through the side tubular members.

Other objects of the present invention will in part be obvious and will in part appear hereinafter.

The invention accordingly comprises the apparatuses, processes and products, together with their parts, steps, elements and interrelationships, that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
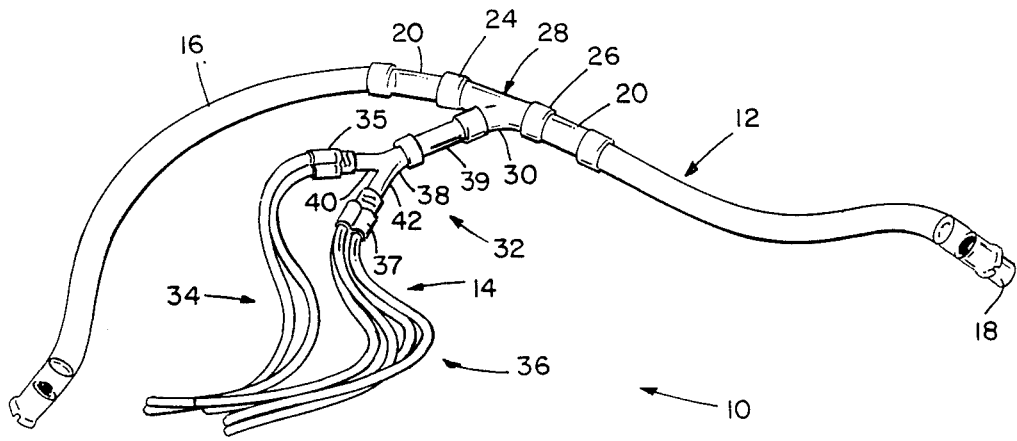
FIG. 1 is a perspective view of an intercostal and lumbar perfusion apparatus embodying the present invention.

Referring now to the drawings, particularly FIG. 1, there is shown an intercostal and lumbar perfusion apparatus 10 embodying the present invention. Intercostal and lumbar perfusion apparatus 10 includes a main member 12 defining a first flow path for providing circulation to distal organs and a plurality of side members 14 defining a second flow path for providing blood flow for intercostal perfusion during aortic surgery.

Figure 2:
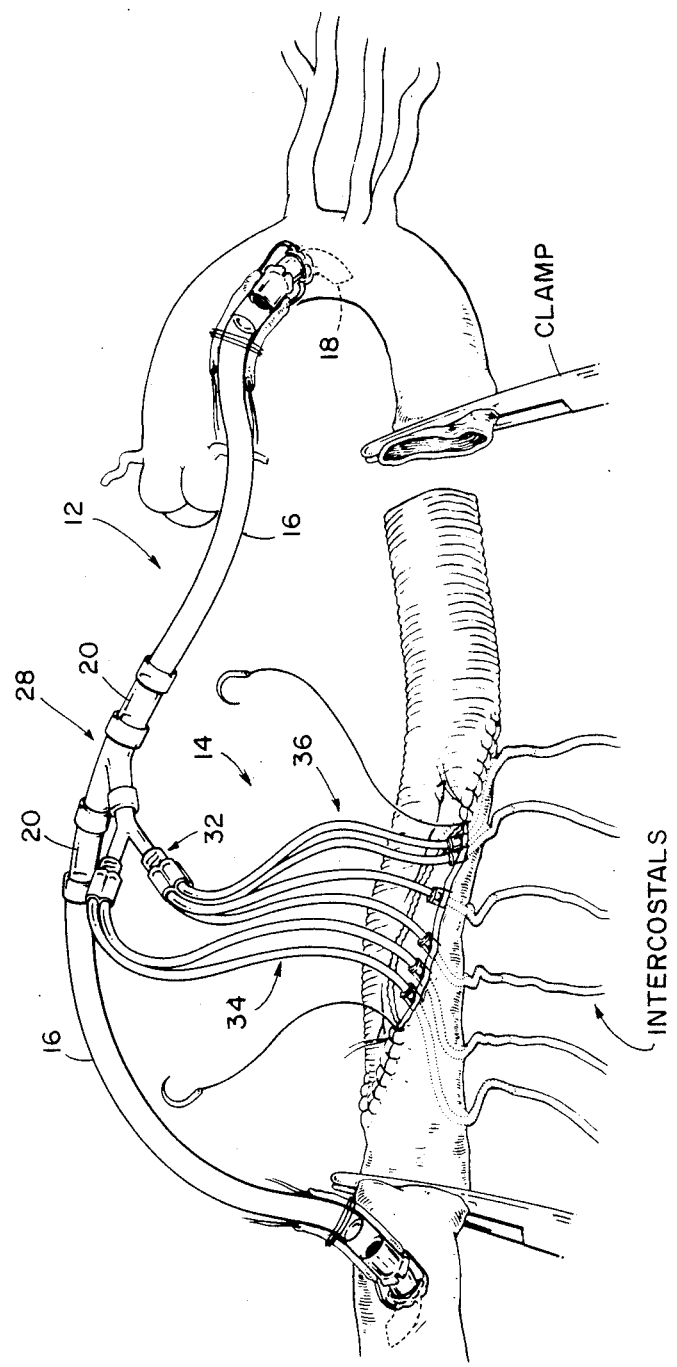
FIG. 2 is a perspective view showing the main member of the intercostal and lumbar perfusion apparatus of FIG. 1 connected proximal and distal to a pathology site and the side member connected to the intercostals.

In the illustrated embodiment, by way of example, main member 12 includes a pair of arterial inflow cannulae 16 having tips 18, and sections of arterial inflow pump tubing 20. In one embodiment, cannulae 16 have an inside diameter of approximately three quarters of an inch and tips 18 have an internal diameter of approximately 8 mm to 10 mm. The working ends or tips 18 of cannulae 16 are configured to be received in the aorta 22 (FIG. 2). The other ends of cannulae 16 and 18 are connected to one end of sections of tubing 20. The other ends of tubing 20 are connected to legs 24,26 of a Y-connector 28. The interconnections of cannulae 16; tubing 20 and Y-connector 28 define the first flow path. The other leg 30 of Y-connector 28 constitutes the start of the second flow path. Y-connector 28 permits a portion of blood flowing in the first flow path to flow into the second flow path while permitting the blood to continue to flow through the rest of the first flow path.

Figure 3:
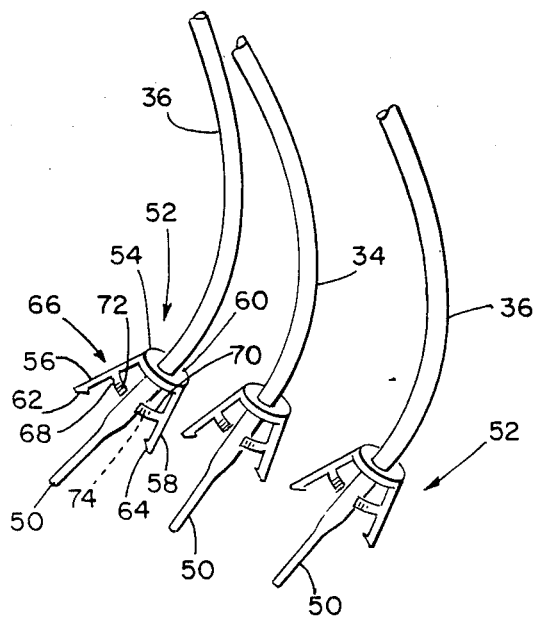
FIG. 3 is a perspective view, somewhat enlarged, of several side members showing their narrowed tips and attached clips.

The second flow path includes a Y-connector 32 that provides two perfusion heads (legs 40,42) and the side members 14 which includes, for example, a plurality of perfusion catheters 34 and 36. Leg 30 of Y-connector 28, Y-connector 32 and side members 14 define the second flow path. A leg 38 of Y-connector 32 is connected to leg 30 of Y-connector 28 by means of a section of tubing 39. The inside diameter of tubing 39 is approximately one quarter of an inch. Catheters 34 and 36 are connected to a leg 40 of Y-connector 32 via a cardioplegia adapter 35 and a plurality of catheters 34 and catheters 36 are connected to the other leg 42 of the Y-connector via a cardioplegia adapter 37. As best shown in FIG. 3, cannulae 34 and catheter 36 have narrowed tips 50 which is sized and shaped to snugly fit into selected intercostal arteries of patients undergoing surgery. Preferably, each narrow tip 50 is a thin-walled member that expands with flow and/or pressure so that the tip is in sealing contact with the inner wall of the intercostal artery into which it is inserted when blood is supplied to the intercostal artery via catheters 34 and 36. The diameter of tips 50 of catheters 34 and 36 is in the range of 1.5 mm to 5.0 mm depending upon the size of the intercostal.

Figure 4:
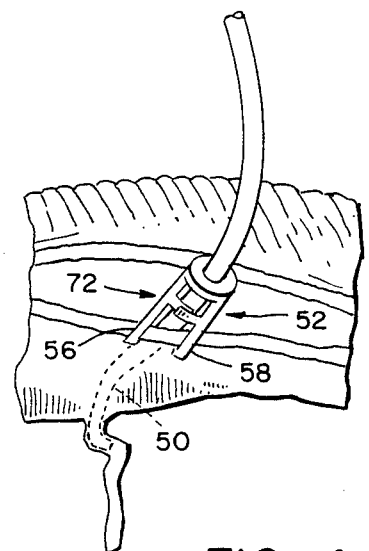
FIG. 4 is a perspective view, somewhat enlarged, of a side member inserted into an intercostal artery and its clip attached to the aorta.

Catheters 34 and 36 are provided with a spring clip 52 which is configured to hold the narrow tip 50 in the intercostal artery. Clip 52 includes a head 54 with a pair of descending legs 56,58 that are normally biased apart as shown in FIG. 3. Legs 56 and 58 are in an opened position when biased apart and in a closed position when locked as shown in FIG. 4. Leg 56 has a hook 62 at its distal end and leg 58 has a hook 64 at its distal end. Hooks 62 and 64 are configured to pierce an artery wall when legs 56 and 58 are squeezed together for clamping or holding catheter 34 or catheter 36 in place when tip 50 is inserted into the intercostal. Head 54 has a central opening 60 that is sized to be captively held on a catheter 36 or a cannula 34. A fastening lock 66 having a pair of interlocking fingers 68 and 70 is provided for holding legs 56 and 58 in their locked position. When legs 54 and 56 are squeezed together, fingers 68 and 70 interlock, by means of teeth 72 and 74, for example. When fingers 68 and 70 are pulled apart, teeth 72 and 74 disengage and legs 54 and 56 spring open to the unlocked position.

In an alternate embodiment of intercostal lumbar perfusion apparatus 10 for use in cases where the number of cardioplegia catheters 34 and 36 shown in FIG. 1 are not needed, Y-connector 32 is not used and tubing 39 is connected directly to cardioplegia adapter 35. A plurality of cardioplegia catheters 34 and catheters 36 are connected to cardioplegia adapter 35.

As hereinafter described, the purpose of intercostal and lumbar perfusion apparatus 10 is to prevent paraplegia caused by ischemia of the spinal cord during aortic surgery, for example surgery on the descending and thoraco abdominal aorta. Main member 12 defines a shunt which circumvents a pathologic section and provides a flow path for circulation to distal organs, the side members 14 provide a flow path for blood flow to the intercostals.

In cases where a shunt cannot be used or the surgeon prefers to use a cardiopulmonary bypass machine (not shown), the arterial inflow cannula of the bypass machine is provided with side members that are similar to side members 14. In this case, the femoral vein is connected to the cardiopulmonary bypass machine and the blood is oxygenated. An arterial inflow line of the bypass machine transports the oxygenated blood to the femoral artery. An alternative technique is to receive the oxygenated blood of the left atrium with tubing and a pump, and pump this blood to the femoral artery. The Y-connector corresponding to Y-connector 28 and its associated side members are connected to the arterial inflow line in a similar manner to the connection side members 14 to main member 12. The associated side members that are connected to the arterial inflow line are used to perfuse the intercostals with oxygenated blood in the manner described in connection with intercostal lumbar perfusion apparatus 10.

The method of the present invention for providing circulation to distal organs and blood flow for intercostal lumbar perfusion during aortic surgery, for example, surgery on the descending and thoraco abdominal aorta, using intercostal lumbar perfusion apparatus 10, includes the steps of attaching the main 12 tubular member to the aorta proximal and distal to a pathologic section in the aorta. The side tubular members 14 are clamped initially to prevent blood from flowing through the side members until the proper sized tips are inserted into the intercostals. The aorta is clamped between the pathologic section and the main tubular member connections so that blood flows to the distal organs through the main tubular members. The aorta is opened to expose the intercostals and the deaired free tips 50 at the ends of the side tubular members 14 are connected to the intercostals. The clamps on the side tubular members are removed so that blood flows to the intercostals through the side tubular members 14 and tips 50. A section of the aorta containing the intercostals is separated and a section is removed from a graft which corresponds to the separated section of the aorta. The separated section of the aorta is attached to the graft in place of the removed graft section and the area about the tubular side members 14 is loosely stitched. The end of the graft is attached to the native aorta, the tubular side members 14 are removed and the loose stitching is tightened. The clamping devices are removed from the aorta while another clamp is placed on the graft beyond the anastomosed patch of aorta containing the intercostals to permit blood flow from the main tubular member 12 to flow through the graft to these intercostals in addition to the distal organs. Finally, the other end of the graft is attached to the aorta, the clamps are removed to allow normal circulation, and then the intercostal and lumbar perfusion apparatus 10 is removed.

In one example of aortic surgery using the lumbar and intercostal perfusion apparatus 10, the sites of the aortic clamps are chosen carefully and the aorta is encircled in such a way that a minimal number of intercostal arteries in the healthy aorta are excluded while enough aortic cuff is provided for anastomosis. The patient is heparinized. Using standard cannulation techniques, the main member 12 is inserted between two points on the aorta proximal and distal to the pathologic segment and then is deaired through the side member 14. The number of intercostals between the two clamps are twice the number of the ribs in this area. Adequate number of intercostal perfusion cannulae 14 are provided and the adequacy of blood flow through them is tested. In practice, the number of intercostals that can be perfused are much fewer than calculated. This is particularly true in the cases of aneurysms, where most of the intercostals are thrombosed. Very small intercostals that do not admit the available catheter tips, especially if the intercostals are on the right side with less chance of spinal cord contribution, are considered insignificant.

Sodium nitroprusside should be started before proximal clamping and titrated for control of proximal hypertension. Application of the clamp should be done in such a way that none of the neighboring intercostals are pinched. Time is recorded when the distal aortic clamp is applied to the aorta. The aorta is opened and the clot is evacuated. The intercostals are examined and sized and the proper size perfusion catheter tips are inserted into the intercostals starting from the distal end.

At first glance, all of the intercostals should be checked for cannulation with a 4 mm cannula. After the proper size cannula has been chosen for an intercostal artery, blood flow should be established through the cannula while it is out of the vessel for deairing and then the flowing cannula is inserted in the appropriate artery. The tips 50 are fixed in place with clip 52 (FIG. 4). At this point, the assistant should make sure the cannulae stay in position, while the surgeon attempts cannulation of other intercostals. If a vessel does not permit the tip of the available catheters, especially if it is a right-sided vessel, it should be left alone temporarily. After adequate intercostal cannulation and securing of catheter tips 50 in place with clips 52, the surgeon will proceed with the operation. Clips 52 are provided for clamping onto the wall of the artery for holding catheters 34 and 36 in the intercostal and preventing their accidentally falling out during the operation.

Cannulation of the posterior intercostals should be done with extreme caution and gentleness. These vessels are very fine and can perforate easily. The direction of these vessels is also variable, but most of the time the directions is lateral and cephalad. Distortion or lengthening of these vessels by the aneurysm or aortic tortuosity is common. Perforation of these vessels can be a source of hemorrhage, as well as a cause for paraplegia. Based on laboratory and clinical experience, the tips 50 of perfusion catheters 34 and 36 are softened and designed to avoid these complications. The time required to perfuse these vessels is only a few minutes. Serial cannulation and reperfusion of major intercostals in a case with multiple intercostals requiring perfusion will minimize the chance of ischemic injury to the spinal cord.

Anastomotic Techniques

Figure 5:
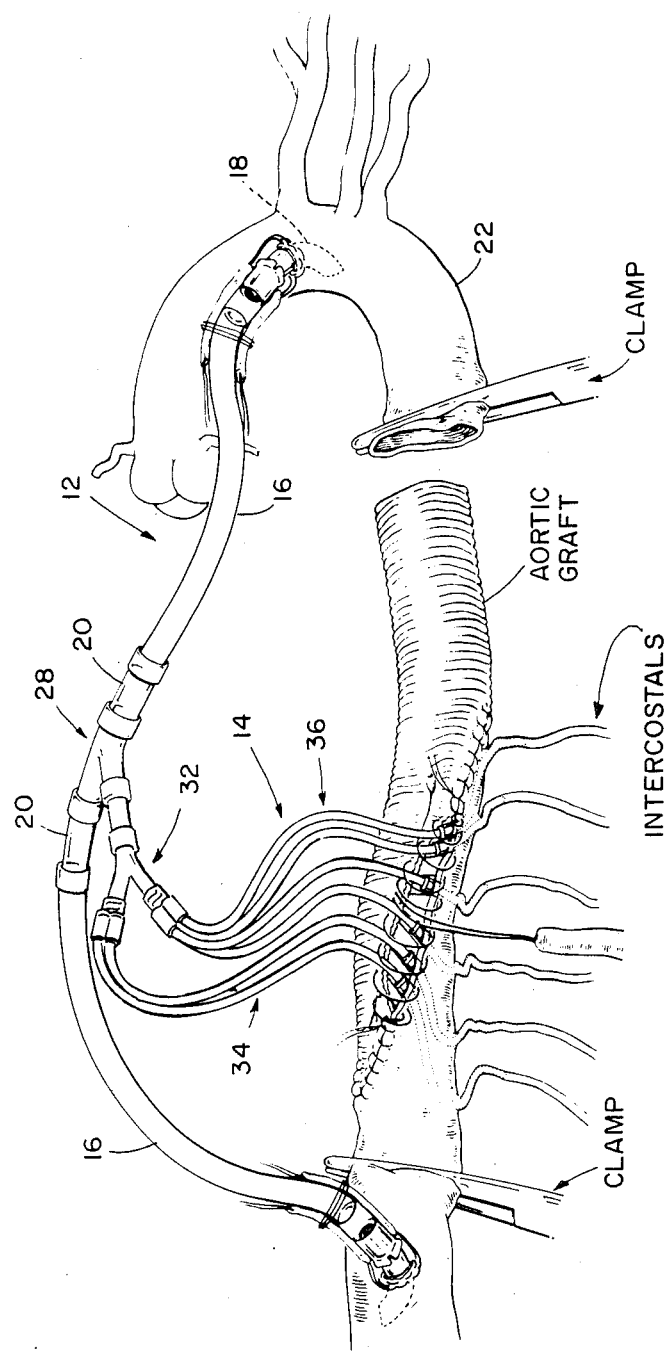
FIG. 5 is a perspective view showing one of the steps in the perfusion of excluded intercostals in a healthy section of the aorta.
Figure 6:
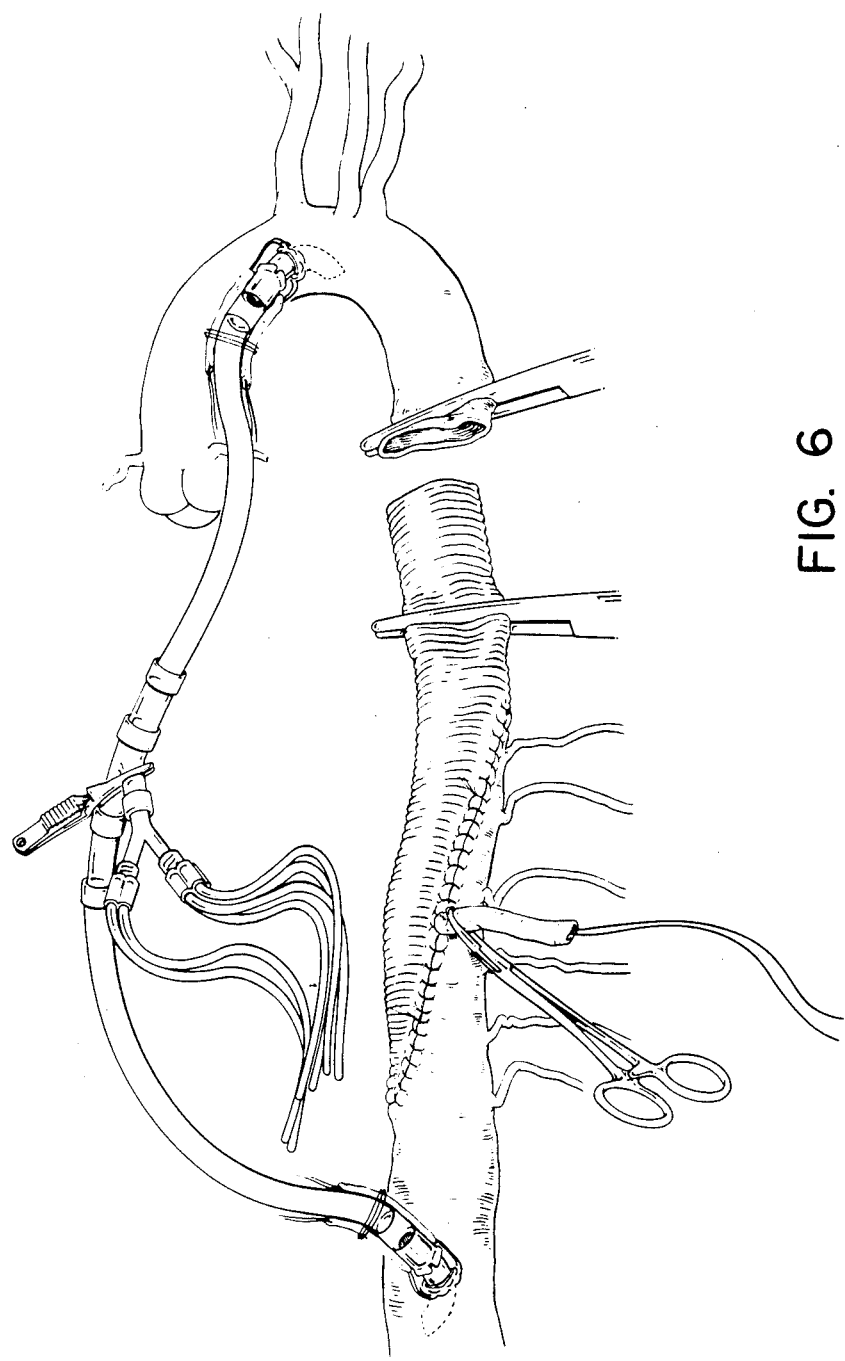
FIG. 6 is a perspective view showing another step in the perfusion of excluded intercostals in a healthy section of the aorta.
Figure 7:
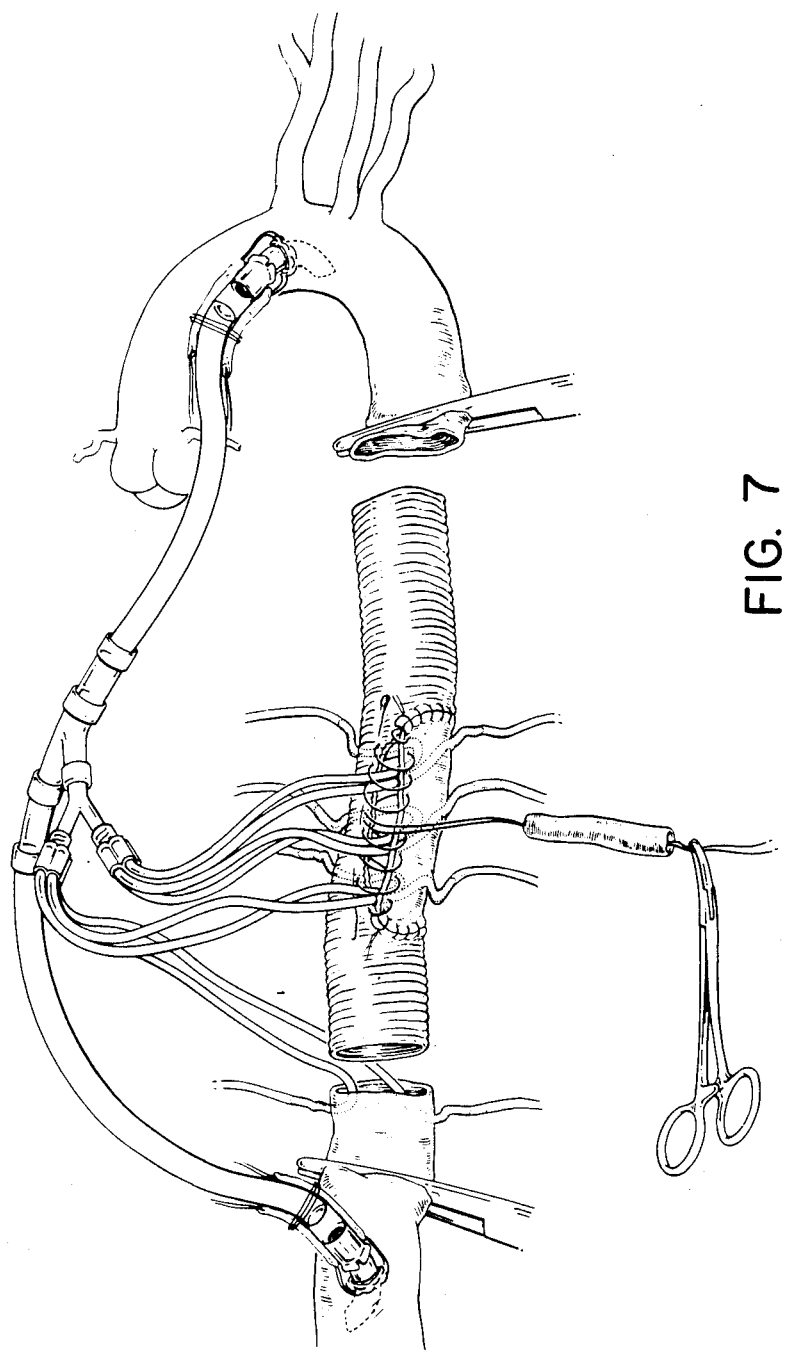
FIG. 7 is a perspective view showing one of the steps in the perfusion of excluded intercostals, some of which are located in an isolated section or island.
Figure 8:
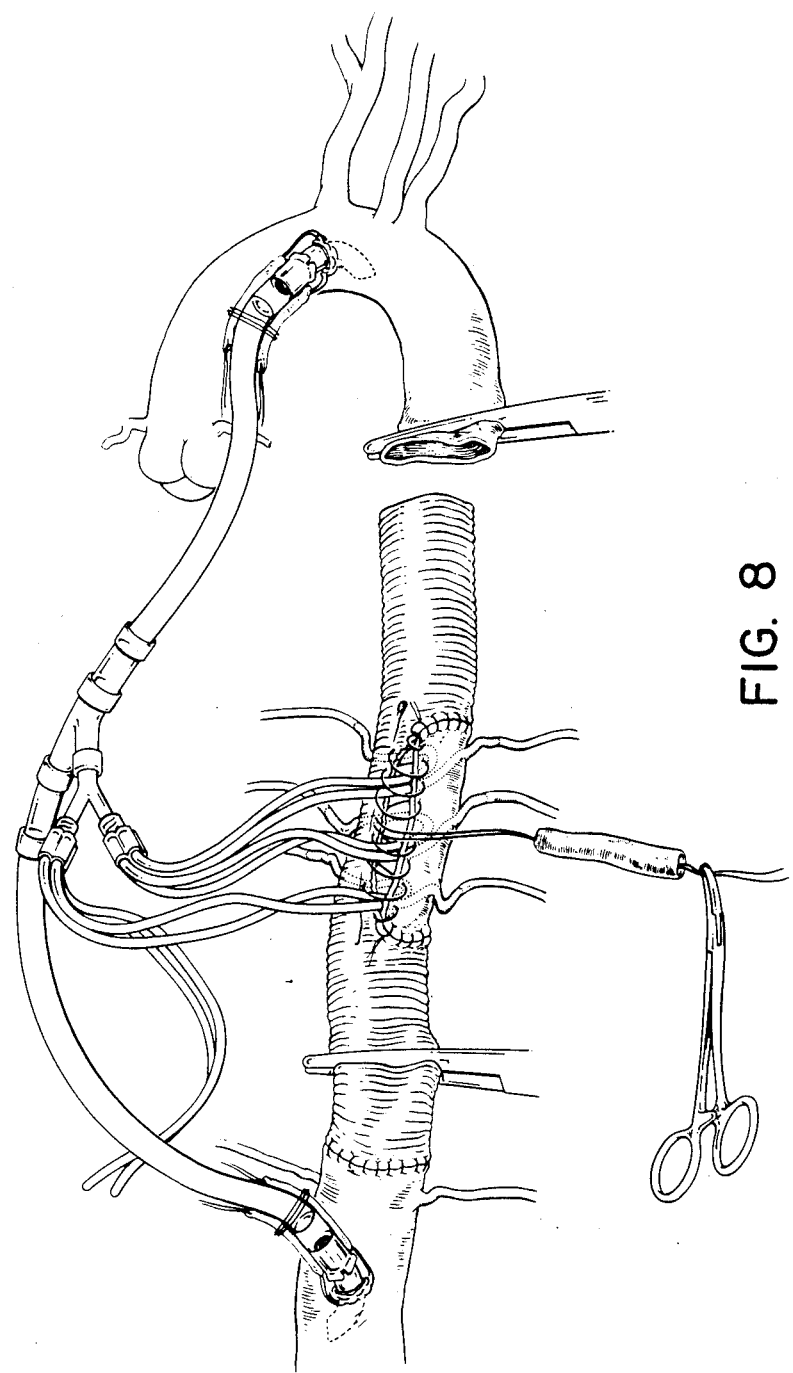
FIG. 8 is a perspective view showing another step in the perfusion of excluded intercostals, some of which are located in an isolated section or island.
Figure 9:
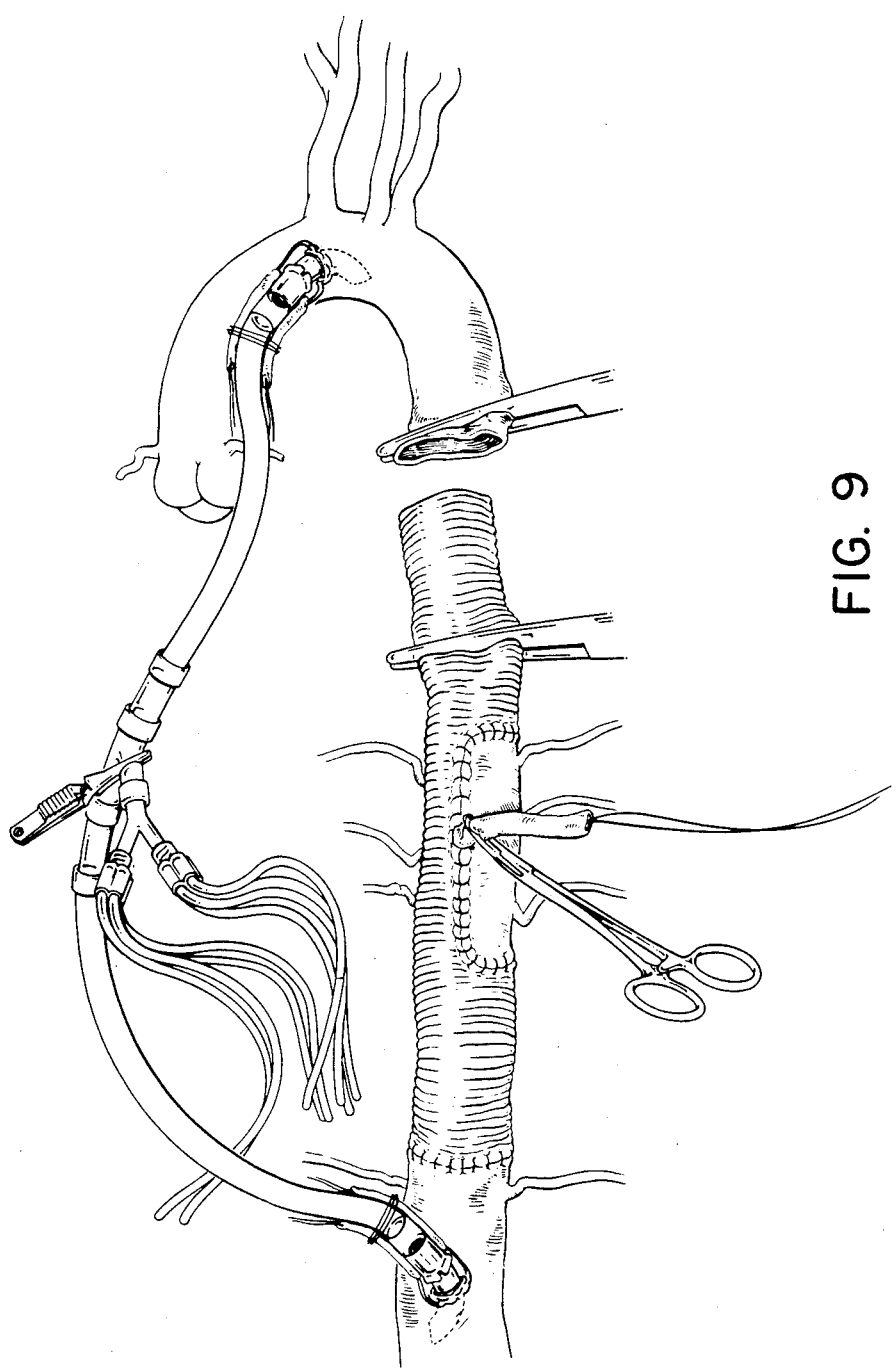
FIG. 9 is a perspective view showing a further step in the perfusion of excluded intercostals, some of which are located in an isolated section or island.

In an example of an anastomotic techniques, FIGS. 7, 8 and 9, the distal anastomosis or the end that has significant perfusing intercostals should be done first. A fabric graft can be preclotted by soaking it in plasma or 5% albumin and, after rinsing the plasma or albumin, it is baked at 300° to 400° for three to four minutes. The end of the graft is tailored in such a way that a tongue of the healthy aortic wall containing the perfusing intercostals is anastomosed to a beveled end of the graft (FIGS. 2, 5 and 6). This anastomosis is done on seventy-five percent of the anastomotic line, leaving a gap of twenty-five percent laterally facing the surgeon (FIG. 2). The perfusing cannulae pass through this gap. The two ends of the suture are tied to secure tightness of the anastomosis. The rest of the anastomosis is completed in open fashion, passing the sutures around and between the perfusing cannulae (FIG. 5).

The anastomosis is completed in the middle of the gap and two ends of the suture are passed through a snare (FIGS. 5 and 7). At this point, the fabric graft is clamped beyond the anastomosis. Through the open anastomosis, the clips 52 holding the catheters in place are released. The cannulae are clamped and removed and while the suture line is tightened with the snare, the aortic clamp next to the anastomosis is released. The graft will be deaired through this anastomosis and using a nerve hook, the anastomosis is tightened and the sutures are tied. It has been found that the ischemic time for this stage is less than a minute. Once the suture line is tied and the hemostasis secured, the other end anastomosis should be done in the usual fashion.

The same technique can be used if an island of posterior wall of the aorta containing perfusing intercostals has to be reimplanted into the side of the aortic graft as shown in FIG. 7. One end of the graft to the aorta anastomosis should be completed first as shown in FIGS. 2-6 before the removal of the perfusing catheters from the intercostals in the reimplanting aortic island. The completed end anastomosis will provide blood flow for these intercostals after removal of the perfusing catheter (FIGS. 7-9).

It is important to reemphasize the precision, gentleness and caution during cannulation and decannulation of the posterior intercostals. These very fine vessels are easily damaged. If the back wall of the aorta is aneurysmal and significant intercostals are coming off this area, extreme care in resection of the rest of the aneurysm should be taken. It is better to circumcise a bottom of the aortic wall containing these vessels than sewing the graft inside the aneurysmal aorta. If the latter technique is used, the sutures could cause potential injury to the intercostals. The sutures can pass around or through the intercostal artery, which can be lengthened by the aneurysm and may be laying by the side of the posterior wall. Also during resection of the aneurysm and tailoring of the posterior patch, extreme caution is warranted. Ignorance of these facts may cause bleeding or even paraplegia. Again, completion of the other end anastomosis should be followed by the release of the other aortic clamp and deairing of the rest of the graft. Then the main member 12 can be removed.

If apparatus 10 is made from conventional plastic materials, the patient must be heparinized before insertion of the apparatus and the heparin can be reversed at this point. Alternately, apparatus 10 can be made from heparin bound material in which case there will be no need for anticoagulation.

Since certain changes may be made in the foregoing disclosure without departing from the scope of the invention herein involved, it is intended that all matter contained in the above description and shown in the accompanying drawing be construed in an illustrative and not in a limiting sense.

What is claimed is:

1. An intercostal lumbar perfusion apparatus for providing circulation to distal organs and blood flow to the intercostals during aortic surgery, said apparatus comprising:
   (a) a main member defining a first flow path, said main member including first and second ends, said first end configured to be connected proximal to a pathological section in the aorta and said second end configured to be connected distal to a pathological section in the aorta, said main member providing adequate circulation of blood distal to the pathological section during aortic surgery when said first and second ends are connected to the aorta;
   (b) a plurality of side members defining a second flow path for providing blood flow for intercostal lumbar perfusion, said side members connected to said main member intermediate said first and second ends thereof, said second flow path communicating with said first flow path, said side members are sized and shaped to be inserted into and snugly fit within the intercostals with minimum resistance to be able to provide adequate blood flow to distal organs; and
   (c) a plurality of clip means operatively connected to said side members, each said clip means including a head and a pair of opposed depending legs, each said depending leg having hooked gripping means for holding said side member in place when said side members are inserted into the intercostals.

2. The intercostal lumbar perfusion apparatus as claimed in claim 1 wherein said depending legs are biased apart, hook means provided at a distal end of each said depending leg, said hook means configured to piece an artery wall when said side members are inserted into the intercostals and said depending legs are squeezed together.

3. The intercostal lumbar perfusion apparatus as claimed in claim 2 including connector means disposed in said first flow path, said connector means having means for permitting a portion of the blood flowing in said first flow path to flow into said second flow path.

4. The intercostal lumbar perfusion apparatus as claimed in claim 3 wherein said connector means includes first Y-connector means having first, second and third leg means, said first and second leg means connected to said main member intermediate the ends thereof, said first and second leg means disposed in said first flow path, said third leg means operatively connected to said side members, said third leg means disposed in said second flow path.

5. The intercostal lumbar perfusion apparatus as claimed in claim 4 wherein said connector means includes second Y-connector means having first, second and third branch means, said first branch means connected to said third leg means, said second and third branch means connected to said side members, said third leg means and said first, second and third branch means disposed in said second flow path.

6. The intercostal lumbar perfusion apparatus as claimed in claim 5 wherein said main member and said side members are tubular members, the diameter of said main member is larger than the diameter of said side members, said side members having narrowed tips that are configured to snugly fit into selected intercostals.

7. The intercostal lumbar perfusion apparatus as claimed in claim 2 including connector means having interconnected first, second and third legs, said first, second and third legs communicating with one another to permit fluid flow therebetween, said first and second legs connected to said main member, said third leg connected to said side members, said first and second legs lying in said first flow path, said third leg lying in said second flow path.

8. The intercostal lumbar perfusion apparatus as claimed in claim 7 wherein main member and said side members are tubular members, the diameter of said side tubular members being smaller than the diameter of said main tubular member, said side members having narrowed tips of selected sizes that are configured to snugly fit into selected intercostals.

9. The intercostal lumbar perfusion apparatus as claimed in claim 2 including locking means for holding said depending legs in their squeezed position.

10. A method for performing aortic surgery and providing circulation to distal organs and intercostal blood flow for intercostal lumbar perfusion during aortic surgery using an intercostal lumbar perfusion apparatus having a main member defining a first flow path and a plurality of intercostal connecting side members defining a second flow path, the side members connected to the main member intermediate the ends thereof, the side members having tips that are selected to interconnect with the intercostals, clips provided on the side members, said method comprising the steps of:
   (a) connecting the ends of the main member to the aorta proximal and distal to a pathologic section in the aorta and shunting the pathology;
   (b) deairing the main member and the side members, and clamping the side members with first clamping means;
   (c) attaching proximal clamping means and distal clamping means to the aorta between the pathologic section and the ends of the main member, said proximal and distal clamping means are positioned adjacent the pathological section so as to include only a minimum number of intercostals between said proximal and distal clamping means;
   (d) longitudinally cutting the pathological section of the aorta between said proximal and distal clamping means to expose the intercostal orifices;
   (e) connecting the tips of the deaired ends of the side members to exposed intercostals and fixing them in place with the clips provided on the side members, removing the first clamping means to permit blood flow through the side members to the intercostals;
   (f) attaching one end of a graft to one of the proximal and distal ends of a healthy section of the cut aorta;
   (g) cutting the aorta about the perfused intercostals;

(h) removing a section of the graft which corresponds to the cut aorta containing the perfused intercostals;

(i) attaching the section of the aorta containing the perfused intercostals to the graft in place of the removed section of the graft and leaving a loosely stitched area about the side members;

(j) clamping the graft between its opened end and the loosely stitched section beyond its attached end;

(k) clamping and removing the side members through the loose stitches and tightening the loose stitching about the graft area, removing the clamping means at the end of the aorta to which the graft has been attached;

(l) attaching the other end of the graft to the other of the proximal and distal ends of the cut aorta so as to form a complete aorta;

(m) removing any remaining clamping means on the aorta and graft and deairing the graft; and (n) removing the main body and closing the opening through which the main body was inserted into the aorta.

11. A method of performing aortic surgery and providing circulation to distal organs and blood flow for intercostal lumbar perfusion during aortic surgery using an intercostal lumbar perfusion apparatus having a main member defining a first flow path and plurality of said members with narrowed tips defining a second flow path, said side members connected to the main member, said method comprising the steps of:

(a) a connecting the main member to the aorta to provide blood flow to organs distal to a pathologic section in the aorta;

(b) deairing and clamping the side members;

(c) clamping the aorta above and below the pathologic section;

(d) cutting the aorta and exposing intercostals in the pathologic section;

(e) rapidly connecting the free ends of the deaired side member tips to the intercostals;

(f) unclamping the side members and permitting blood to flow into the intercostals;

(g) attaching one end of a graft to the cut aorta;

(h) removing a section of the graft that corresponds to the cut section of the aorta which contains the intercostals; and (i) attaching the section of the aorta containing the intercostals to the graft in place of the removed section of the graft.

12. An intercostal lumbar perfusion apparatus for use with a cardiopulmonary bypass machine or a left atrial to femoral bypass machine for providing circulation to distal organs and blood flow to the intercostals during aortic surgery, the apparatus comprising:

(a) a main member configured to be interconnected with an arterial inflow line of a cardiopulmonary bypass machine or the femoral line to the left atrial to femoral bypass machine, said main member defining a first flow path through which blood flows from the cardiopulmonary bypass machine or left atrial to femoral bypass machine for providing circulation to organs distal of a pathologic section of the aorta;

(b) at least one side member connected to said main member and configured to connect with the intercostals, said side member defining a second flow path for providing blood flow for intercostal lumbar perfusion, each said side member sized and shaped to be connected to an intercostal, said second flow path communicating with said first flow path, a quantity of blood flowing in said first flow path and through said main member flowing into said second flow path and through said side member;

(c) a plurality of clip means operatively connected to said side members, each said clip means including a head and a pair of opposed depending legs that are biased away from each other, each said depending leg having hooked gripping means for holding said side members in the intercostal artery, said clip means configured to hold said side members in the intercostal artery; and (d) connector means disposed in said first and second flow paths, said connector means having means for directing blood flowing in said first flow path into said second flow path.

13. The intercostal lumbar perfusion apparatus as claimed in claim 12 including a plurality of intercostal connecting side members having tips, each said tip being sized and shaped to interconnect with a selected one of the intercostals.

14. The intercostal lumbar perfusion apparatus as claimed in claim 13 wherein said intercostal connecting side members include a plurality of cannulae that are sized to fit into selected intercostals.

15. The intercostal lumbar perfusion apparatus as claimed in claim 14 wherein said tips have a diameter that is in the range of 1.5 mm to 5.0 mm.

16. The intercostal lumbar perfusion apparatus as claimed in claim 13 wherein said intercostal connecting side members include a plurality of cannulae and a plurality of tipped catheters having narrowed and thin walled tips that are sized to fit into selected intercostals.

17. The intercostal lumbar perfusion apparatus as claimed in claim 16 wherein said tips have a diameter that is in the range of 1.5 mm to 5.0 mm.

18. A method for performing aortic surgery and providing circulation to distal organs and blood flow for intercostal lumbar perfusion during aortic surgery using an intercostal lumbar perfusion apparatus having a main member defining a first flow path and plurality of side members with narrowed tips defining a second flow path, said side members connected to the main member, said method comprising the steps of:

(a) connecting the main member to the aorta to provide blood flow to organs distal to a pathologic section in the aorta;

(b) deairing and clamping the side members;

(c) clamping the aorta above and below the pathologic section by attaching clamping means to the aorta between the pathologic section and the two ends of the main member;

(d) cutting open the aorta and exposing the excluded intercostals;

(e) rapidly connecting the free ends of the deaired side member tips to the exposed intercostals;

(f) unclamping the side members and permitting blood to flow into the intercostals;

(g) attaching one end of a graft to the cut aorta;

(h) removing a section of the graft that corresponds to the cut section of the aorta which contains the intercostals; and (i) attaching the section of the aorta containing the intercostals to the graft in place of the removed section of the graft and leaving a loosely stitched area about the side members, and then finishing the anastomosis and advancing the aortic clamp so that blood flow to the intercostals is switched from the side members to the main member, whereby blood flow is not interrupted.

* * * * *